US00PP28506P3

(12) United States Plant Patent
Maillard et al.

(10) Patent No.: US PP28,506 P3
(45) Date of Patent: Oct. 10, 2017

(54) PEACH TREE NAMED 'SWEETEMBER'

(50) Latin Name: ***Prunus persica* (L.) Batsch**
Varietal Denomination: SWEETEMBER

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 38 days.

(21) Appl. No.: 14/757,158

(22) Filed: Nov. 27, 2015

(65) Prior Publication Data

US 2016/0157401 P1 Jun. 2, 2016

(30) Foreign Application Priority Data

Nov. 27, 2014 (QZ) ..... PBR 2014/3163

(51) Int. Cl.
*A01H 5/08* (2006.01)

(52) U.S. Cl.
USPC ..... Plt./195

(58) Field of Classification Search
USPC ..... Plt./195
See application file for complete search history.

*Primary Examiner* — Keith Robinson
(74) *Attorney, Agent, or Firm* — Westerman, Hattori, Daniels & Adrian, LLP

(57) ABSTRACT

A new and distinct variety of white peach tree denominated 'SWEETEMBER' has fruits with high eating quality and very long shelf life without alteration before and after harvesting, with a semi-sweet greenish white flesh, with a slightly star-shaped red pigmentation around the stone cavity and into the stone cavity, and an attractive luminous and homogenous skin with a high percentage of luminous purple red blush on skin surface.

2 Drawing Sheets

Botanical classification: *Prunus persica* (L.) Batsch.

Variety denomination: 'SWEETEMBER'.

This application claims priority of Community plant variety right No. 2014/3163 filed on Nov. 27, 2014 (Nov. 27, 2014) which is hereby incorporated by reference in its entirety.

BACKGROUND OF THE NEW VARIETY

The present invention relates to a new and distinct variety of white peach tree, *Prunus persica* (L.) Batsch, which has been given the variety denomination 'SWEETEMBER'. This new tree produces fruits with a long shelf life without alteration both on the tree after growth completion and after harvesting, very good eating quality, clingstone white and slightly green flesh fruits for fresh market in September in the Pyrénées-Orientales department, France. Contrast is made to 'MAILLARDIVA' white peach tree (non patented), for reliable description. 'SWEETEMBER' is a promising candidate for commercial success in that it has very attractive fruits with very long shelf life without alteration both before and after harvesting.

ORIGIN OF THE VARIETY

The 'SWEETEMBER' white peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'SWEETEMBER' variety resulted from a pollinated cross between the 'NECTAPI' (U.S. Plant Pat. No. 21,156) yellow nectarine tree, which was used as the seed parent, and the 'SWEETPRIM' (U.S. Plant Pat. No. 21,157) white peach tree which was used as the pollen parent.

The 'SWEETEMBER' variety was obtained by hybridizing and propagated by grafting on a "INRA® GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'SWEETEMBER' white peach tree blooms at the end of February or during March near Elne in the Pyrénées-Orientales department, France.

More particularly, it blooms between February 21st and March 24th generally slightly earlier than 'MAILLARDIVA' white peach tree (non patented). The blooming period is considered medium to late. However, it was observed that its early date of blooming seems to be highly dependant on climatic conditions.

The first fruit of 'SWEETEMBER' ripens generally during September, approximately 5 to 7 days after the ripening of the fruits of 'MAILLARDIVA' white peach tree (non patented). More particularly, it usually ripens between August 28th and September 26th. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Due to chemical development, processing and printing, the leaves and fruit depicted in these photographs may or may not be accurate when compared to the actual botanical specimen.

Figure 1:
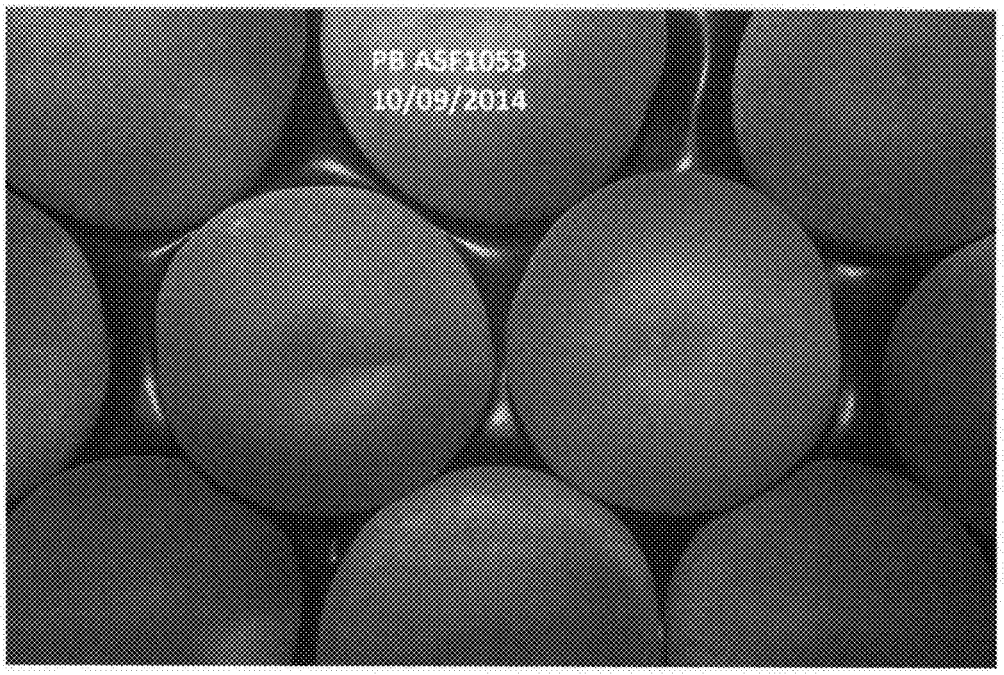
FIG. 1 is a color photograph that shows a close view of typical fruits of the new variety 'SWEETEMBER' at ripening time.
Figure 2:
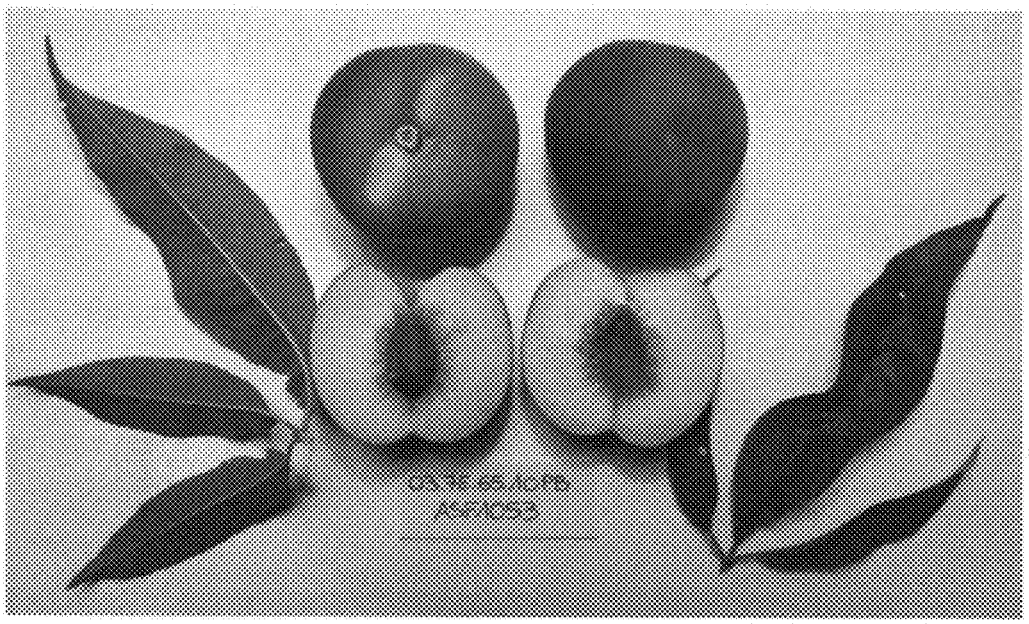
FIG. 2 is a color photograph which shows the leaves of the variety and four typical specimens of the fruit, two having been cut in half with the pit being left into one of the halves for depicting fruit flesh and pit of the new variety.
Figure 3:
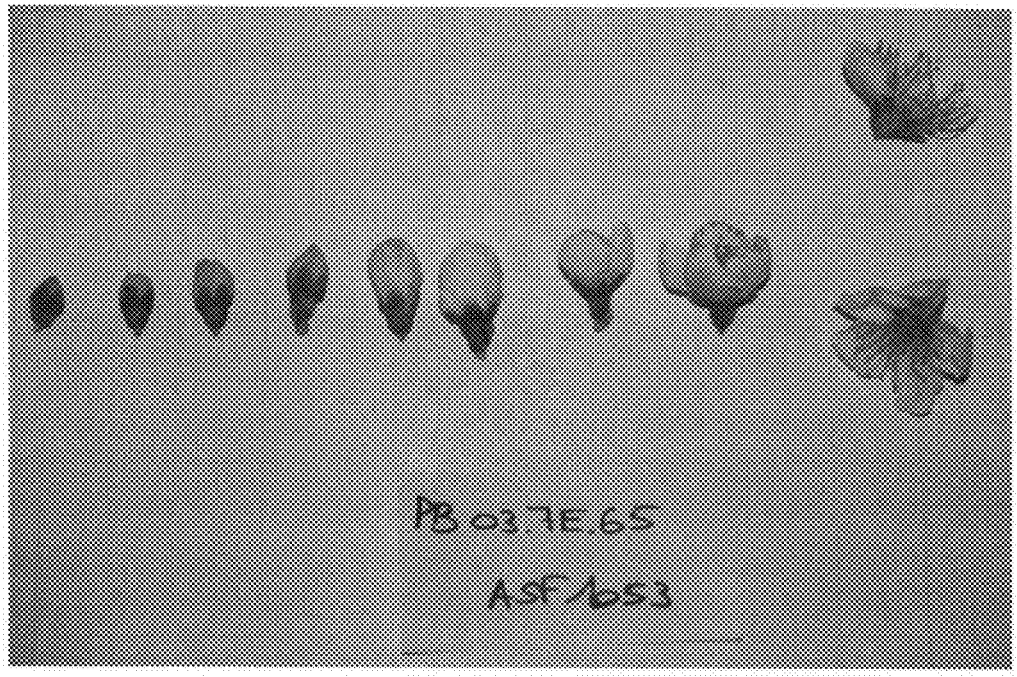
FIG. 3 is a color photograph which depicts the flower buds at different development stages, and the reverse and side view of the flower and the reproductive organs with petals removed, of the new variety.
Figure 4:
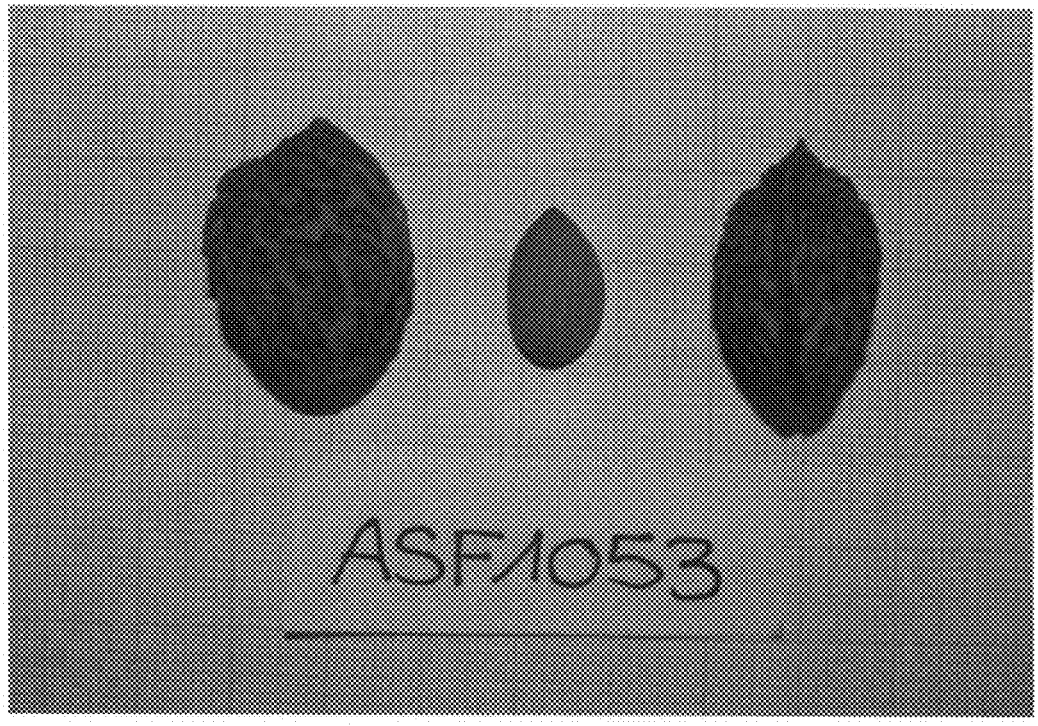
FIG. 4 is a color photograph different views of the stone of the new variety and the kernel of the stone.

In FIGS. 1 to 4, the new variety named 'SWEETEMBER' is identified with the breeder's reference 'ASF1053'.

DETAILED BOTANICAL DESCRIPTION

The tree, flowers, and fruit may vary in slight detail due to variations in soil type, cultural practices, and climatic condition. The potential for commercial production of fresh fruits by 'SWEETEMBER' is high, due to fruit very long shelf life without alteration after harvesting.

Trees are medium vigorous and large stature half-standing in a semi-flared to semi-upright out aspect. The anthocyanic coloration of flowering shoot is present excluding brushwood side away from sun. The time of beginning of flowering is considered medium to late; flowering begins at the end of February or in March. The type of flower is showy with medium petal size. Petals are pale pink. Leaf glands are present and round. The fruit flesh is white and slightly green generally with a red pigmentation into the stone cavity and around this cavity, in a star shape. The fruit skin is very thick, with a luminous and homogenous red purple blush on a red background. The stone is clingstone and his size is small to medium. Fruit taste is semi-sweet, very aromatic and with a high level of sugars.

Compared to 'MAILLARDIVA' white peach tree (non patented), which has a time of beginning of flowering considered late, 'SWEETEMBER' variety shows a medium to late period of flowering, as set forth above. The first fruits of 'SWEETEMBER' variety ripen 5 to 7 days later than the fruits of 'MAILLARDIVA'. The fruits of 'MAILLARDIVA' show a slightly triangular shape, whereas the fruits of 'SWEETEMBER' are very round and regular in shape. The size of 'SWEETEMBER' fruits is higher than the size of 'MAILLARDIVA' fruits. The flavour of the fruit flesh for 'SWEETEMBER' is considered semi-sweet, sugary and aromatic. In comparison, the flavour of the flesh for the variety 'MAILLARDIVA' is considered balanced.

Compared to its female parent, which is 'NECTAPI' (U.S. Plant Pat. No. 21,156) yellow nectarine tree, the new variety 'SWEETEMBER' is a white peach tree. Moreover, 'SWEETEMBER' is considered as a late to very late-season of maturity whereas 'NECTAPI' is considered to be a medium to late-season variety. The leaf glands of 'SWEETEMBER' are round-shaped whereas the leaf glands of 'NECTAPI' are reniform.

The new variety male parent, which is 'SWEETPRIM' (U.S. Plant Pat. No. 21,157), is also a white peach tree. The new variety 'SWEETEMBER' has a late to very late period of ripeness whereas the variety 'SWEETPRIM' is considered as an early-season variety for consumption. More particularly, the fruits of 'SWEETPRIM' ripen in June whereas the fruits of 'SWEETEMBER' ripen generally during September. The variety 'SWEETPRIM' produces fruits having a flesh of balanced to semi-sweet flavour. In comparison, the fruits of 'SWEETEMBER' are semi-sweet, sugary and aromatic. Finally, the white flesh of 'SWEETPRIM' shows an important red pigmentation and is then considered as a 'half-blood' peach. In comparison, the greenish white flesh of the new variety 'SWEETEMBER' has a slightly star-shaped red pigmentation around the stone cavity on approximately 10.0 millimeters and a red pigmentation into said cavity.

DETAILED DESCRIPTION

Referring more specifically to the pomological details of this new and distinct variety of white peach tree, the following was observed on trees in their fifth growing season (fourth year of production) for trees, fruits, leaves and stone and in their fourth growing season (third year of production) for flowers, under the ecological conditions prevailing at the orchards located near the town of Elne, Pyrénées-Orientales departement, France. All observations have been done on rootstock cultivars. Used rootstocks were "INRA® GF677" trees. All major color code designations are by reference to The R.H.S. Colour Chart (Fourth Edition published in 2001) provided by The Royal Horticultural Society of Great Britain.

Tree:

*Size*.—Generally. — Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm including current season shoots length. The tree size is consistently reduces to 250 cm the next years.

*Spread*.—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered strong. Probably useful to reduce the supply in nitrogen nutriments in order to avoid an excessive vegetation.

*Productivity*.—Very Productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

*Bearer*.—Very regular. The fruit distribution is considered homogenous on mixed branches and spurs having more than 1 year. A reduced thinning is performed, regarding the ability of the new variety to produce homogenous fruits having an interesting potential in terms of size.

*Form*.—The 'SWEETEMBER' variety has naturally a semi-flared to semi-upright shape.

*Density*.—Considered dense.

*Hardiness*.—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

Trunk:

*Diameter*.—Approximately 5.2 to 6.5 centimeters in diameter when measured at a distance of approximately 30 centimeters above the soil level.

*Bark texture*.—Considered slightly rough, with lenticels.

*Lenticels*.—Numerous lenticels are present. The number of lenticels reaches 2 or 3 lenticels per $cm^2$. The lenticels range in size from approximately 4.0 millimeters to 6.0 millimeters in width, and from 2.0 to 2.5 millimeters in height.

*Lenticel color*.—The outside of lenticels has a silver-grey color (RHS Grey 201 D), whereas the inside is considered brown (RHS Greyed Orange 163 A).

*Bark coloration*.—The bark has a silver-grey color (RHS Grey 201 C) slightly darker than the outside of lenticels color.

Branches:

*Size*.—Mature branches and current season shoots are considered medium to large for the variety.

*Diameter*.—Average as compared to other peach varieties. The current season shoots have a diameter from 5.0 to 7.0 millimeters, and mature branches have a diameter from 10.0 to 13.0 millimeters.

*Surface texture*.—Average, wood which is several years old has no furrowed appearance.

*Crotch angles*.—Primary branches are considered variable, but the crotch angles are generally between 50 degrees and 60 degrees from the horizontal axis. This particular characteristic is not considered distinctive of the variety, however.

*Current season shoots.—Internode length: Generally between* 22.0 and 27.0 millimeters. Color of mature branches: Medium brown (RHS Grey Brown 199 A).

*Current seasons shoots*.—Color. — The color of new shoot tips is considered a pale yellow-green (RHS Yellow Green 145 A) on lower part of new shoot tips, whereas the upper part is darker and colored in red purple (RHS Greyed Purple 187 A).

Leaves:

*Size*.—Considered large for the species. The ratio leaf length/leaf width is 3.48.

*Leaf length*.—Approximately 157.0 to 186.0 millimeters with leaf petiole. The medium length is 171.8 millimeters.

*Leaf width*.—Approximately 40.0 to 62.0 millimeters. The medium width is 49.3 millimeters.

*Leaf base shape*.—Concave.

*Leaf form*.—Lanceolate.

*Leaf tip form*.—Short, pointed and acuminate.

*Leaf color*.—Upper leaf surface. — Dark Green (RHS Green 137 A). Lower surface. — A lighter green (RHS Green 137 C) than the upper leaf surface color.

*Leaf texture*.—Smooth and glabrous on both surfaces of the leaves.

*Leaf venation*.—Pinnately veined.

*Mid-vein*.—Color. — Light green, almost yellow (RHS Yellow Green 145 D). The color may evolve with maturity.

*Leaf margins*.—Slightly undulating.

*Form*.—Considered slightly dentate.

*Uniformity*.—Leaves are isolated or grouped by 2 or 3. In this last case, one leaf of normal size is found with one or two smaller leaves (at least 50% smaller).

*Leaf petioles*.—Size. — Considered medium to small. Length. — About 9.0 to about 12.0 millimeters. Diameter. — About 1.5 to 2.0 millimeters.

*Petioles color*.—Upper petiole surface. — Green (RHS Green 143 C) or light green (RHS Yellow Green 144 A). Lower surface. — Light green (RHS Yellow Green 144 C or RHS Yellow Green 145 A).

*Leaf glands*.—Size. — Considered medium. Their length is about 0.9 to 1.1 millimeters and their width is about 0.9 to 1.1 millimeters. Number. — Generally 2 to 3 glands per leaf. Type. — Round. Color. — On young leaves, leaf glands color is considered a light green (RHS Green 145 B). On older leaves, leaf glands color turns to a dark brown (RHS Grey Brown 199 A to RHS Grey Brown 199 B). Margins. — Smooth and regular.

*Leaf stipules*.—Generally. — No leaf stipules were observed. But as seen in the characteristic relative to the leaves uniformity, it is possible to find leaves by groups of 2 or 3, with a normal-size leaf and smaller ones.

Flowers:

*Flower buds*.—Generally. — At pre-floral stage of development, the floral buds are conic in form with a slightly pointed tip. Their form is evolving until blooming, with variable dimensions. Just before blooming, floral buds are approximately 9.0 millimeters wide and approximately 13.0 millimeters long. Color. — This characteristic is dependent upon the proximity to bloom. At pre-floral stage of development (stage A), the bottom of the flowers buds, formed by the sepals, is of purple-brown color (RHS Greyed Purple 183 A to RHS Greyed Purple 183 B to RHS Greyed Purple 183 C to RHS Greyed Purple 183 D and RHS Grey Brown Group 199A at the base). The corolla, formed by the petals, is generally of pale to medium pink color (RHS Red Purple 65 A to RHS Red Purple 65 C). Petals color shows an evolution until the end of flowering.

*Hardiness*.—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—The blooming time generally begins at the end of February or early in March. The first bloom was observed on Feb. 24, 2011.

*Blooming time*.—Considered medium to late-season in relative comparison to other commercial peach cultivars grown in the Pyrénées-Orientales departement, France. The date of full bloom is observed at the middle of the blooming period. The date of bloom varies slightly with climatic conditions and cultural practices. Thus the first full bloom was observed on February 24$^{th}$ until Mar. 6, 2011 then from March 15$^{th}$ until Mar. 24, 2012, then from February 26$^{th}$ to Mar. 15, 2013, then from February 21$^{st}$ until Mar. 4, 2014 and then from March, 11$^{th}$ until Mar. 19, 2015.

*Duration of bloom*.—Approximately 10 to 18 days. This characteristic varies slightly with the prevailing climatic conditions.

*Flower type*.—The variety is considered to have a showy type flower (rosette type).

*Flower size*.—Considered medium. Flower diameter at full bloom is approximately 36.0 to 39.0 millimeters.

*Bloom quantity*.—Considered medium to abundant, approximately between 35 and 40 flowers per meter, with a good distribution and a high rate of fruit set.

*Flower bud frequency*.—Generally 2 flower buds appear per node, occasionally 1.

*Petal size*.—Generally. — Considered medium.

*Length*.—Generally 18.12 millimeters (between 16.0 to 20.0 millimeters).

*Width*.—Generally 16.37 millimeters (between 15.0 to 19.0 millimeters).

*Petal form*.—Round-shaped.

*Petal count*.—Generally 5.

*Petal texture*.—Smooth, soft and glabrous on both surfaces of the petals.

*Petal color*.—Both surfaces of the petal are colored with a pale Pink (RHS Red Purple 69 B to RHS Red Purple 69 C) when young, becoming slightly darker until the end of blooming.

*Fragrance*.—Sweet.

*Petal claw*.—Form. — The claw is considered to have a conic form, with a slightly curved tip. Length. — Approximately 6.0 millimeters. Width. — Approximately 5.0 millimeters.

*Petal margins*.—Generally considered wrinkled and very wavy, sinuate.

*Petal apex*.—Generally. — The petal apices are generally round-shaped and slightly pointed.

*Flower pedicel*.—Length. — Considered medium to large and having an average length of approximately 3.5 millimeters. Diameter. — Considered average, approximately 2.0 millimeters. Color. — Yellow grey (RHS Greyed Yellow 160 A).

*Calyx*.—Internal surface texture. — Smooth and glabrous. Color. — At the stage F of blooming, when the flower is open, the inner surface of the calyx is matt and considered greenish yellow (RHS Yellow Group 13 A to RHS Yellow Group 13 B or RHS Yellow Green 150 A to RHS Yellow Green 150 A). The outer surface of the calyx is considered of purple-brown color (RHS Greyed Purple 183 A to RHS Greyed Purple 183 B to RHS Greyed Purple 183 C to RHS Greyed Purple 183 D).

*Sepals*.—Form. — Ovate. Number. — Generally five sepals. Surface texture. — The outer surface has a short, fine pubescent texture. The inner surface of the sepals is smooth. Size. — Average. Color. — At the stage F of blooming, the inner surface of the sepals is matt and considered greenish yellow (RHS Yellow Group 13 A to RHS Yellow Group 13 B or RHS Yellow Green 150 A to RHS Yellow Green 150 A). The outer sides of sepals are colored with a matt Red (RHS Greyed Purple 183 A to RHS Greyed Purple 183 B to RHS Greyed Purple 183 C to RHS Greyed Purple 183 D and RHS Grey Brown 199A at the base).

*Average number of stamens per flower*.—Approximately 39 stamens per flower.

*Anthers*.—Generally. — Medium to large in length (approximately 1.0 millimeter). The position of the stigma is below compared to the anthers. Color. — Orange yellow color (RHS Yellow Orange 16 A to RHS Yellow Orange 16 B) or red to red orange color (RHS Greyed Purple Group 178 A) when the maturity is passed.

*Pollen production*.—Pollen is abundant, and has an orange yellow color (Approximately RHS Yellow Orange 17 B to RHS Yellow Orange 17 C) which may evolve with maturity. The present variety is considered auto-fertile (self-pollinating).

*Filaments*.—Size. — Medium length, between 8.0 and 13.0 millimeters in length. Filaments length is generally higher to the pistil's length.

*Color*.—Considered light pink (approximately RHS Red Purple 62 C to RHS Red Purple 62 D) or pink slightly darker (RHS Red Purple 73 A to RHS Red Purple 73B). The color becomes darker during the blooming.

*Pistil*.—Number. — Usually 1, sometimes more than 1. Generally. — Average in size. Length. — Approximately 16.0 millimeters including the ovary. Generally equal to stamen length, if not slightly smaller. Color. — Considered a very pale green (RHS Yellow Green 150 D or RHS Yellow Green Group 151 D). The color evolves during the blooming. Surface texture. — Glabrous. Pubescence of the ovary. — Present.

Fruit:

*Maturity when described*.—Very firm in ripe conditions (shipping ripe).

*Date of first picking*.—Sep. 20, 2010.

*Date of last picking*.—The date of harvest varies slightly with the prevailing climatic conditions. The 'SWEETEMBER' variety has a late to very late date of picking, and a grouped maturity. The maturity is grouped within 5 to 9 days and the harvest is generally performed in two runs. Last known picking times carry on September 20$^{th}$ to Sep. 26, 2010, then from August 28$^{th}$ to Sep. 4, 2011, then from September 14$^{th}$ to Sep. 18, 2012, then from September 18$^{th}$ to Sep. 26, 2013, and then from September 2$^{nd}$ to Sep. 10, 2014 and then from September 8$^{th}$ to Sep. 19, 2015.

*Size*.—Generally. — Homogeneous in size, mainly size 2A, round in shape, slightly flattened, regular, very little downy.

*Average cheek diameter*.—Approximately 74.0 to 78.0 millimeters.

*Average axial diameter*.—Approximately 63.0 to 67.0 millimeters.

*Typical weight*.—Generally about 180.0 to 200.0 grams. This characteristic is high dependent upon the prevailing cultural practices, and therefore is not particularly distinctive of the variety.

*Fruit form*.—Generally. — Round slightly flattened. The fruit is generally uniform in symmetry, viewed from the suture's plane.

*Fruit suture*.—Wide-mouthed and slightly marked, extending from the base to the apex. No apparent callousing or stitching exists along the suture line. Not pointed.

*Suture*.—Color. — The suture has generally a similar color to the whole fruit color, a luminous purple red (RHS Greyed Purple N186 A or RHS Greyed Purple 187 A).

*Ventral surface*.—Form. — Smooth.

*Apex*.—Non-prominent, generally slightly depressed.

*Base*.—Semi-flared, shallow.

*Stem cavity*.—Average depth of the stem cavity is about 12.0 to 15.0 millimeters. Average width is about 20.0 to 22.0 millimeters.

*Fruit skin*.—Thickness. — Considered very thick and strong, and the adherence of skin to flesh is strong to medium, depending on the fruit maturity. Texture. — Glabrous, with a short pubescence. Taste. — Semi-sweet, aromatic, with a high level of sugars. Tendency to crack. — None observed.

*Color*.—Blush color. — This blush color is a luminous and homogenous purple red (RHS Greyed Purple N186 C or RHS Greyed Purple 187 A). The red blush covers 75% to 80% of the fruit skin surface on a red to a washed red background (RHS Red 46 A to RHS Red 46 B). The percentage of the blush on the fruit skin surface can vary, and is generally dependant upon the prevailing conditions under which the fruit was grown. Ground color. — The ground color covers approximately 20 to 25% of the fruit skin surface, and the color is considered red to washed red (RHS Red 46 A to RHS Red 46 B).

*Fruit stem*.—Medium in length, approximately 7.0 to 8.0 millimeters.

*Diameter*.—Approximately 4.0 millimeters.

*Color*.—Pale green (RHS Yellow Green 145 A to RHS Yellow Green 145 B).

*Flesh*.—Ripens. — Very homogenously, slowly. The flesh has a long shelf life. Texture. — Very firm, very dense, crunchy, melting, juicy at harvest maturity stage. Fibers. — Not fibrous. Aroma. — Pronounced. Eating quality. — Considered very good and aromatic. Flavor. — Considered semi-sweet and very aromatic. The Brix is generally superior to 10 and acidity comprised between 6 and 9 meq/100 ml. Juice. — Very juicy at complete maturity. Brix. — Generally 11.0 to 16.5 degrees. This characteristic varies slightly with the number of fruit per tree; prevailing cultural practices; and the surrounding climatic conditions. Flesh color. — The flesh is white, slightly green (RHS Green White 157 C) usually with a red pigmentation (RHS Red 46 A) into the stone cavity and around the stone cavity in about 10 millimeters, in a star shape.

Stone:

*Type*.—Clingstone, more or less adherent depending on the fruit maturity.

*Size*.—Considered small to medium to large for the variety. The stone size varies significantly depending upon the tree vigor, crop load and prevailing growing conditions.

*Length*.—Approximately 27.0 to 28.0 millimeters.

*Width*.—Approximately 20.0 to 21.0 millimeters.

*Diameter*.—Approximately 16.0 to 17.0 millimeters.

*Form*.—Straight.

*Base*.—Round to slightly oblique.

*Apex*.—Shape. — The stone apex is short, pointed.

*Stone cavity*.—Considered small to medium size, with an ovate-form and dimensions corresponding to the stone's dimensions (i.e. approximately 27.0 to 28.0 millimeters in length, approximately 20.0 to 21.0 millimeters in width and approximately 16.0 to 17.0 millimeters in diameter).

*Stone surface*.—Surface texture. — The pit is transversely furrowed on its entire surface. Furrows are more pronounced toward the apex. The stone is pitted toward the base. Relief is prominent generally and present basally. Ridges. — The surface texture is generally characterized by more prominent ridges along the ventral edges and is more prominent at the apical tip.

*Ventral edge*.—Width. — Considered small to medium, and having a dimension of approximately 1.5 to 2.0 millimeters at mid-suture.

*Dorsal edge*.—Shape. — Grooved.

*Stone color*.—The color of the dry stone is generally considered light orange brown (RHS Greyed Orange 164 B or RHS Greyed Orange 164 C).

*Tendency to split*.—Splitting is very low or absent, depending on climatic conditions between blooming period and stone hardening.

*Kernel*.—Size. — The kernel is considered medium. Length. — Approximately 16.0 millimeters. Width. — Approximately 10.0 millimeters. Thickness. — Approximately 6.0 millimeters. Form. — Considered elliptic and flattened. Pellicle. — The pellicle of the kernel has a short pubescence. Color. — The kernel skin is a orange-brown (RHS Greyed Orange 164 A). The almond, which is the seed of the kernel, is white (RHS White 155 B) and has a bitter taste. The kernel and its embryo are mature at the time of fruit maturity.

*Use*.—The subject variety 'SWEETEMBER' is considered to be a peach tree of the late to very late season of maturity, and which produces fruits that are considered firm, attractively colored with a very luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

*Keeping quality*.—Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

*Shipping quality*.—Considered very good. The fruit of the new white peach variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

*Resistance to insects and disease*.—No particular susceptibilities were noted. The present variety is not sensitive to powdery mildew, or conservation diseases and decay due to its thick and strong skin. More particularly, the variety 'SWEETEMBER' is not sensitive to *Taphrina deformans*, the causal agent of peach leaf curl. 'SWEETEMBER' is also not sensitive to *Podosphaera pannosa* which is responsible for the powdery mildew of peach. The new peach variety 'SWEETEMBER' is not sensitive to aphids (belonging to the superfamily of Aphidoidea), in particular the green peach aphids *Myzus persicae* and the black peach aphids *Brachycaudus persicae*. Also, the 'SWEETEMBER' variety is not sensitive to acari.

Although the new variety of peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of white peach tree as illustrated and described, characterized by fruits with high eating quality and very long shelf life without alteration before and after harvesting, with a semi-sweet greenish white flesh, with a slightly star-shaped red pigmentation around the stone cavity and into the stone cavity, and an attractive luminous and homogenous skin with a high percentage of luminous purple red blush on skin surface.

* * * * *